(12) United States Patent
Tamirisa

(10) Patent No.: US 10,532,186 B2
(45) Date of Patent: Jan. 14, 2020

(54) NEUROVASCULAR PUNCTURE-AVOIDANT SHEATH

(71) Applicant: Kris V. Tamirisa, La Jolla, CA (US)

(72) Inventor: Kris V. Tamirisa, La Jolla, CA (US)

( * ) Notice: Subject to any disclaimer, the term of this patent is extended or adjusted under 35 U.S.C. 154(b) by 0 days.

(21) Appl. No.: 15/170,113

(22) Filed: Jun. 1, 2016

(65) Prior Publication Data

US 2017/0348508 A1    Dec. 7, 2017

(51) Int. Cl.
| | | |
|---|---|---|
| *A61M 25/01* | (2006.01) | |
| *A61B 17/34* | (2006.01) | |
| *A61M 25/06* | (2006.01) | |
| *A61M 19/00* | (2006.01) | |
| *A61B 90/00* | (2016.01) | |

(52) U.S. Cl.
CPC ..... *A61M 25/0108* (2013.01); *A61B 17/3401* (2013.01); *A61B 17/3403* (2013.01); *A61B 17/3496* (2013.01); *A61M 19/00* (2013.01); *A61M 25/0612* (2013.01); *A61B 2017/3413* (2013.01); *A61B 2090/3925* (2016.02)

(58) Field of Classification Search
CPC ........ A61M 5/3295; A61M 2005/3112; A61M 2005/1583; A61M 2005/1585; A61M 2005/1586; A61M 25/0643; A61M 2205/195; A61M 2025/0086; A61M 2025/009

See application file for complete search history.

(56) References Cited

U.S. PATENT DOCUMENTS

| | | | | |
|---|---|---|---|---|
| 4,230,123 A * | 10/1980 | Hawkins, Jr. | ...... | A61B 10/0283 600/435 |
| 5,048,530 A * | 9/1991 | Hurwitz | ............... | A61B 8/0833 600/461 |
| 5,364,373 A * | 11/1994 | Waskonig | .......... | A61B 17/3401 604/117 |
| 5,484,423 A * | 1/1996 | Waskonig | .......... | A61B 17/3401 604/239 |
| 5,527,273 A * | 6/1996 | Manna | ............. | A61B 17/22012 604/22 |
| 5,593,393 A * | 1/1997 | Trudell | ............... | A61F 9/00772 604/264 |
| 5,669,882 A * | 9/1997 | Pyles | ................. | A61B 17/3401 604/158 |
| 5,871,470 A * | 2/1999 | McWha | ............. | A61B 17/3401 604/158 |
| 6,368,299 B1 * | 4/2002 | Cimino | ............ | A61B 17/22012 601/2 |
| 6,565,542 B2 * | 5/2003 | Kumar | ............... | A61B 17/3401 604/104 |
| 7,204,820 B2 * | 4/2007 | Akahoshi | ............ | A61F 9/00745 604/22 |
| 2006/0100653 A1 * | 5/2006 | Akahoshi | ............ | A61F 9/00745 606/169 |
| 2006/0206055 A1 * | 9/2006 | Ice | ..................... | A61B 17/3401 604/164.01 |

(Continued)

*Primary Examiner* — Quynh-Nhu H. Vu
(74) *Attorney, Agent, or Firm* — Donn K. Harms

(57) ABSTRACT

A device and method for a guidance sheath is provided which is configured to prevent laceration or puncture of nerves, blood vessels and surrounding tissue, during positioning of a coaxially located needle employed for various medical procedures, such as, the administration of an anesthetic blockade, neuromonitoring, electromyography or a therapeutic intervention.

18 Claims, 2 Drawing Sheets

(56) References Cited

U.S. PATENT DOCUMENTS

| | | | |
|---|---|---|---|
| 2006/0253056 A1* | 11/2006 | Kadziauskas | A61F 9/00745 |
| | | | 602/22 |
| 2008/0065018 A1* | 3/2008 | Racz | A61M 25/007 |
| | | | 604/164.01 |
| 2011/0015562 A1* | 1/2011 | Akahoshi | A61M 1/008 |
| | | | 604/22 |
| 2011/0045055 A1* | 2/2011 | Hingston | A61L 31/088 |
| | | | 424/424 |
| 2014/0018732 A1* | 1/2014 | Bagaoisan | A61M 25/0136 |
| | | | 604/95.04 |

* cited by examiner

NEUROVASCULAR PUNCTURE-AVOIDANT SHEATH

BACKGROUND OF THE INVENTION

1. Field of the Invention

The present invention relates to a device and method employed during the provision of regional anesthesia. More particularly the disclosed device and method relate to a guidance sheath which is configured to prevent laceration or puncture of nerves, blood vessels and surrounding tissue, during positioning of a coaxially located needle employed for various medical procedures, such as, the administration of an anesthetic blockade, neuromonitoring, electromyography or a therapeutic intervention. Further the unique tip renders the device more easily discerned for position and angle when viewed on a display screen using electronic medical imaging.

2. Prior Art

In the practice of local or regional anesthesia, a physician administers anesthesia to a specific body region. Such is regularly practiced during surgery, or for relief of pain subsequent to surgery, or as a means for extended pain relief due to trauma or chronic pain caused by disease. In many surgical cases, a local or regional anesthesia is preferable to general anesthesia because of increased safety. Further, the ability of a local blockade continues after such surgery as a means to control postoperative pain control.

During the administration of local or regional anesthesia, the physician delivers a local anesthetic in close proximity to a target or nerve plexus. When precisely placed, a neural blockade is established to eliminate or significantly reduce sensed pain by the patient in the area of the delivered local aesthetic.

Electrical nerve stimulation in the past has been a commonly used method for localizing or discerning target nerves, prior to the injection of local anesthetic. Such electrical nerve stimulation during local or regional anesthesia employs electrical stimulus delivered by a needle to obtain a defined response (muscle twitch or sensation). In this fashion, the physician is able to observe and locate a peripheral nerve or nerve plexus desired with electric pulses communicated by a needle which cause localized patient movements.

In more recent years, ultrasound has been employed by physicians during needle placement. In such procedures an ultrasound generating device generates viewable depictions of the interior of the body of the patient, and concurrently shows the needle or probe device and its location. Some physicians may use one means, for determining nerve location, or the other and in many case physicians will uses both means for determining if the distal end of the anesthetic delivery needle is properly placed to anesthetize the desired nerve or body location for the procedure.

Once the nerve or locale for injection has been determined, relative to the needle, a determined amount of a local anesthetic is communicated to a delivery point in close proximity to the determined nerve site to block nerve conduction and thereby provide a sensory and motor block for surgery and/or, eventually, analgesia for pain management.

Such needle delivered electrical nerve stimulation can be used for a single-injection technique, as well as to provide guidance during a subsequent insertion of for example a continuous nerve block catheter.

However, successful provision of regional anesthesia is particularly dependant upon the accurate placement of the needle providing electrical impulses, as well as the subsequent positioning of the needle communicating the anesthetic, proximate to the target nerve or nerves. Further, whether it be the delivery of anaesthesia drugs to the determined site, or the communication of electrical stimulation prior to such drug delivery, needles employed for both such instances must be accurately moved through body tissue and placed both to determine and to anesthetize the plexus or target site.

As a consequence of the need to move a pointed object through body tissue during such procedures, the potential for injury to adjacent nerves, blood vessels, and body tissue from the sharp point of the needle delivering the electrical stimulus, as well as the drug delivery needle or catheter, continues to be a significant risk factor to the patient.

Probing and drug delivery procedures using elongated needle or similar instruments have the potential to cause significant harm to the patient. Such can easily occur from unintended punctures and lacerations to surrounding nerves and blood vessels. While the risk of such injury may reduce in relation to the skill of the physician, such is not eliminated since the physician is using two dimensional sound generated images, and reflex reactions, and cannot actually view potential delivery site for the needle point, which is being translated within the body of the patient. While probes with coverings have been employed by medical professionals to help reduce the potential for harm, conventional needle sheaths themselves have been known to themselves cause internal injury to delicate nerves and blood vessels adjacent an intended anesthetic delivery site.

As such, there is a continuing and unmet need for a device which overcomes the noted shortcomings of conventional art. Such a device should be adapted to surround a needle employed for medical procedures such as, for example, a procedure for delivery of local anaesthesia, and so positioned, reduce the chance of puncture or laceration of nerves and blood vessels and body tissues during the positioning of a sharp needle point at a determined location. Such a device should be easily employed with existing needles and other elongated drug delivery devices and the like employed for such procedures to thereby insure widespread use. Still further, such a device should be configured to provide enhanced location determination using ultra sound generated video positioning systems.

SUMMARY OF THE INVENTION

The device herein disclosed and described achieves the above-mentioned goals through the provision of an elongated sheath, which is adapted to engage upon and surround, a needle while being advanced into the body tissues of a patient. The elongated sheath has an axial cavity communicating between a first opening providing a lumen adapted for an engagement with a needle base having a needle extending into the axial cavity.

The sheath has a second opening adapted for translation of the distal end of the needle located in the lumen defined by the axial passage, to project from the second opening when triggered. A drug delivery needle in an engaged configuration within the axial cavity of the surrounding sheath, is thus shielded from contact with nerves, blood vessels and the tissue of the patient, during positioning of the sheath and coaxially positioned needle at a blockade site.

Further, the sheath may also be employed upon a nerve block needle used for nerve stimulation to prevent tissue and nerve damage during locating the needle to communicate an electric charge to a nerve.

Particularly preferred in all modes of the device herein, is the formation of the distal end of the sheath, in a bulbous shape, relative to the linear cylindrical shape of the sheath extending from the first end to the bulbous distal end. The bulbous shaped portion of the sheath, at the distal end and adjacent an annular recess depending into the circumference of the exterior surface of the body of the sheath, is preferably sized with a diameter at a smallest, which adapted to allow passage of the needle axially through the second opening located at the distal end.

The largest diameter of the spherical portion is to equal or slightly less than the diameter of the cylindrical portion of the body of the sheath running from the annular recess toward the first end of the sheath. Currently a diameter of the spherical portion having an diameter to yield a circumference of the spherical portion between fifty to ninety five percent of the circumference of the first or cylindrical portion of the body of the sheath is preferred for a number of reasons noted herein.

The bulbous portion at the distal end of the sheath, positions a highly curved distal end to communicate with the tissues of the patient during advancement of the needle covered by the sheath therethrough. This is unlike the pointed, or straight cylindrical walled sheaths or covers conventionally in use. The highly curved area of the spherical portion, extending radially from the second opening, back to the annular recess, positions curved surfaces facing all tissue contacting the distal end of the sheath during use. No matter the direction of movement of the distal end of the sheath, the patient tissue will contact a curved surface.

Conventional sheaths or shrouds lack such a smooth curved contact surface radially extending from the second opening. Instead such conventional devices present a forward facing sidewall or the like which can itself cut or lacerate patient tissue during advancement and positioning in the patient.

An additional advantage found with the bulbous portion adjacent an annular recess during ultrasonography assisted guided positioning, or fluoroscopically guided positioning, or computed tomography guided positioning, is a more easily discerned location of the distal end of the needle-surrounding sheath, within the body of the patient. The spherical portion or bulbous shape at the distal end of the sheath, adjacent the annular recess, provides the physician with certainty as to the location of the distal end of the sheath with all such sound and RF-aided positioning, which create video depictions of the body interior.

This spherical portion or bulbous shape is viewable from a wide variety of angles by the physician with certainty as to the location of the distal end of the sheath relative to surrounding tissues. This is unlike a conventional cylindrical shaped sheaths or covers which employ a linear sidewall surrounding an opening at the second end which is hard to ascertain in angled 2D views which occur frequently in the two dimension video depicted viewing noted above. Consequently, it has been found the physician can more easily determine the angular portioning of the axis of the sheath and needle, with the bulbous or substantially spherical portion and recess at the distal end since with practice the angular position can be discerned by viewing the tissue through the annular recess direction of the bulbous portion during movement.

The sheath disclosed herein, is adapted to connect in an engaged position, to surround any needle or elongated device, being advanced into a patient. In this engaged position the sheath protects the nerves, blood vessels and tissues of a patient from the needle, and helps eliminate lacerations or punctures caused by the points and exposed edges of the cylindrical openings of conventional needle-surrounding sheaths and the like. Further, so engaged coaxially with a needle, the device provides enhanced viewing on electronically generated images and easy visual determination of the distal end of the sheath or sheath at a wide variety of angular views, because the novel spherical portion adjacent the annular recess, is easily discernable on video screens of depicting images generated by sonic, RF, or computer-aided positioning devices. Further, the sheath may be surfaced with angular indentations rendering it more visible during an ultrasound guided procedure, or a polymeric coating having hollow nano microspheres encapsulated in the cured material, such as microspheres from Cospheric Innovations of Santa Barbara, Calif.

The sheath device herein can be adapted to engage and surround a wide variety of needles, or other elongated delivery devices which must be positioned within the body of a patient with a high degree of precision such as noted above. So engaged the device concurrently provides the protection from puncture and laceration, as well as improved viewing using electronic and sonic generated images. It should be noted that the sheath device herein is employable with both human and animal patients. Consequently, the description herein focusing upon needles employed for positioning at a target or nerve plexus in humans, should not be considered limiting in scope.

With respect to the above description, before explaining at least one preferred embodiment of the herein disclosed needle shielding and positioning sheath invention in detail, it is to be understood that the invention is not limited in its application to the details of construction and to the arrangement of the components in the following description or as illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based, may readily be utilized as a basis for designing of needle surrounding structures, methods and systems for carrying out the several purposes of the present disclosed device. It is important, therefore, that the claims be regarded as including such equivalent construction and methodology insofar as they do not depart from the spirit and scope of the present invention.

It is an object of the invention to provide a needle surrounding sheath, which adapted for an engagement to surround needles being positioned in a patient.

It is another object of the invention to provide such a sheath, which has a substantially spherical or bulbous portion positioned at the distal end, radially surrounding a second opening for translation of a coaxial positioned needle therethrough.

It is a further object of the invention to provide a such a needle surrounding sheath, in which the spherical portion or bulbous portion at a second end and adjacent an annular recess, provides enhanced viewing and distal end position determination on electronically generated views thereof.

Further objects of the invention will be brought out in the following part of the specification, wherein detailed description is provided for the purpose of fully disclosing the invention but without placing limitations thereon.

BRIEF DESCRIPTION OF DRAWING FIGURES

DETAILED DESCRIPTION OF THE PREFERRED EMBODIMENTS OF THE INVENTION

Figure 1:
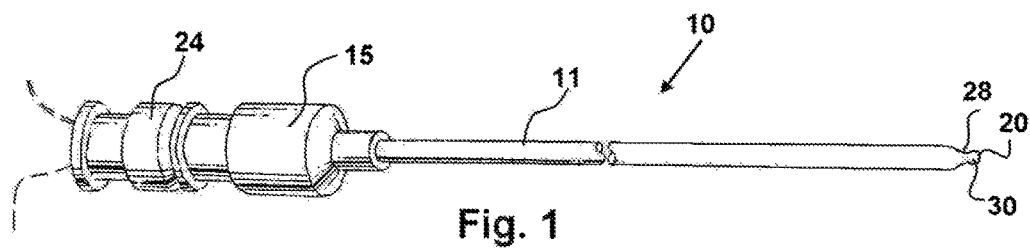
FIG. 1 depicts the device herein in an engaged position with the sheath surrounding a needle positioned within an axial passage therein, and a substantially spherical portion positioned at distal end, adjacent an annular recess.
Figure 2:
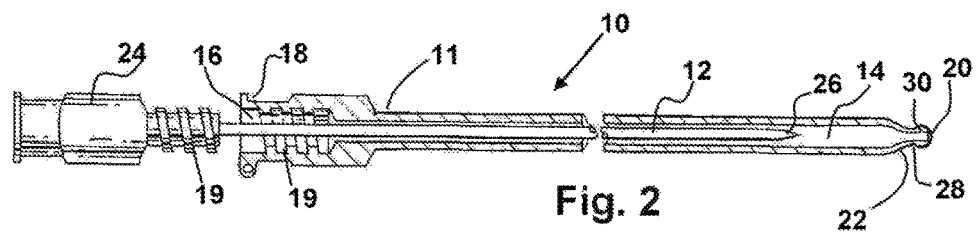
FIG. 2 shows a sectional view of the device similar to that of FIG. 1, having a first end adapted for removable or other operative engagement with a body engaged at a first end of a needle extending into the axial passage of the body forming the sheath.

Now referring to drawings in FIGS. 1-6, wherein similar components are identified by like reference numerals, there is seen in FIGS. 1-2, the sheath device 10 herein in an engaged position, wherein the elongated cylindrical body 11 of the sheath or device 10 surrounds a needle 12 extending axially through an axial passage 14 of the cylindrical body 11 of the device 10. The axial passage 14 communicates between a first opening 16 at a first end 18 of the cylindrical body 11 of the sheath device 10, to a second opening 20 located at a distal end 22 thereof.

As shown, a first end 16 of the body of the body 11 of the sheath device 10 is adapted to operatively engage with a handle 24 or similar component which is engaged to a first end of the needle 12 to position the needle totally withing the axial passage 14. Such an engagement may be sliding between the two or for instance cooperative threads on the body 11 and the handle 24 or frictional engagement.

This of the body 11 at the first end 18 thus is adapted to engage the body 11 to the handle 24 of the needle, in a manner whereby manipulation of the handle 24, while holding a grip 15 or other part of the sheath device 10, will translate the needle 12 within the axial passage 14, and thereby translate the distal end 26 of the needle 12, to project through and extend from the second opening 20.

Particularly preferred in all modes of the device 10 herein, is a substantially spherical portion 30 positioned at or adjacent the distal end 22 of the body 11 of the sheath device 10 opposite the first end 18 thereof. Also preferred adjacent to the spherical portion 30 is an annular recess 32 in-between a larger linear first portion of the body 11 of the sheath device 10, and the spherical portion 30 at the distal end 22 of the body 11 defining the sheath device 10.

By substantially spherical is meant any globular or flattened spherical shape, or similar modified spherical shape, which when positioned on the distal end 22 of the body 11 of the sheath device 10, will position a curved surface on the distal end 22 which radially extends from and around the second opening 20, and if present, to an annular recess 28 in-between the spherical portion 30 and a linear first portion of the body 11 of the sheath device 10 extending from the annular recess 28 toward the first end 18 thereof.

Thus the substantially spherical portion 30 can be round like a globe, or for example be egg-shaped, almond shaped, "blimp" shaped, or otherwise bulbous shaped, having the curved surface extending radially around and away from the second opening 20, and if present, continuing to and intersection of the curved surface of the spherical portion 30, with the annular recess 28. Thus a substantially spherical shape or bulbous curved shape, which positions a curved surface extending around and radially from the second opening 20, toward the first end 18 of the body 11 or toward and intersecting and edge of the annular recess 28, is considered within the scope of this patent.

While it is noted that a spherical portion 30 can be placed at the distal end of the body 11 without the annular recess 28, to inclusion of the recess 28 is preferable. The substantially curved shape of the spherical portion 30 and the adjacent annular recess 28, in addition to significantly reducing lacerations and punctures of tissue as noted above, provides a significantly enhanced view on an electronic display, of the distal end 22 location of the body 11 of sheath device 10 when it is used with ultrasound, RF, or computer aided depictions of the sheath device 10 within the body of a patient.

Figure 3:
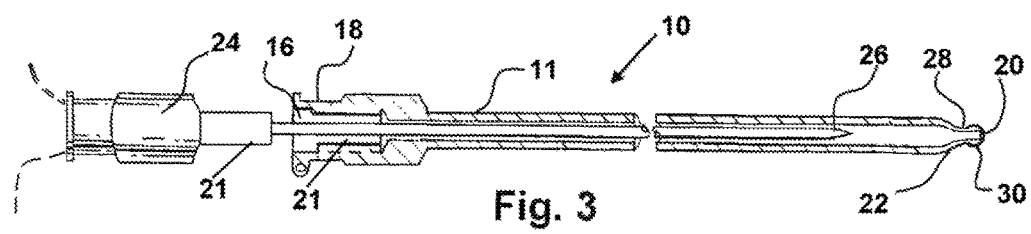
FIG. 3 depicts the device herein in a similar fashion to that of FIG. 2, and showing the first end in another configuration adapted for operative engagement with the body engaged to a first end of the needle.

As noted, shown in FIG. 2 shows a sectional view of the sheath device 10 similar to that of FIG. 1, having a first end 18 of the body 11 forming the sheath device 10, adapted for operative engagement with a handle 24 engaged to a first end of the needle 12. As depicted in FIG. 2 and FIG. 3, this operative engagement allows the user to manipulate the handle 24 relative to the body of the sheath 11 which remains fixed in position, and to translate the distal end of 26 of the needle 12 to extend from the second opening 20, or retract the needle 12 entirely back into the axial passage 14.

In FIG. 2, this operative engagement is a threaded engagement between threads 19 on the handle 24 and mating threads 19 on the first end 18 of the body 11 of the sheath device 10. In FIG. 3, this engagement is shown as a frictional or sliding engagement of mating surfaces 21 of the handle 24 with a complimentary mating surface 21 at the first end of the body 11 of the sheath device 10. The depicted modes of operative engagement allow manipulation of the handle 24 relative to the body 11 to axially translate the needle 12 along the axial passage 14 to thereby extend the distal end of the needle, from the second opening 20.

Figure 4:
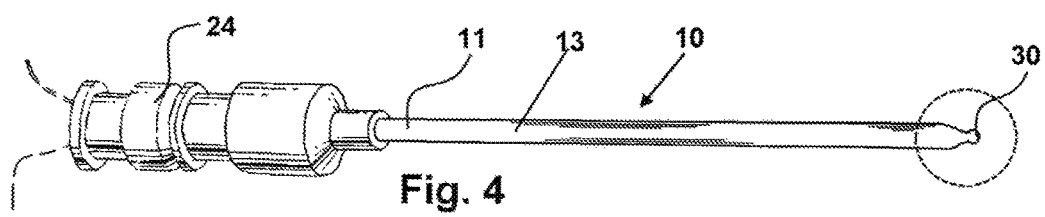
FIG. 4 shows the device in a similar fashion to that of FIG. 1, and depicts the second end having the substantially spherical portion adjacent an annular recess, which is encircled by dotted line referring to the enlarged shapes of FIGS. 4a and 4b and 4c.

As can be seen in FIG. 4, all modes of the sheath device 10 include the substantially spherical portion 30 positioned on the distal end 22 of the body 11, adjacent to an annular recess 28. This spherical portion 30 as shown in FIG. 4, is encircled by dotted line which refers to the enlarged shapes of substantially spherical portions 20 shown in FIGS. 4a and 4b and 4c. These depictions are exemplars of current preferred configurations of substantially spherical shapes of the spherical portion 30, but which should not be considered limiting as noted herein.

Figure 4A:
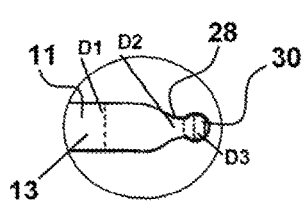
FIG. 4a shows a substantially spherical portion with an elongated globe-like or substantially circular shape having a curved surface radially communicating around and away from the second opening, toward the annular recess which is positioned in-between a first linear portion of the body of the sheath and the spherical portion. Also shown are the three diameters D1, D2, and D3.

FIG. 4a depicts a spherical portion 30 with a round or more globular spherical shape, which formed on the distal end 22 positions a curved surface which radially communicates around the second opening 20, and toward the annular recess 28. In all modes the annular recess 28 is positioned in-between the spherical portion 30 and the linear first portion 13 of the body 11 of the sheath device 10 extending from the first end 18 to the annular recess 28.

Also shown in FIG. 4a are the diameter of the first portion 13 of the body 11 of the sheath device 10, extending from the annular recess 28 toward the first end 18 of the body 11, and the diameter D2 of the annular recess 28, and the diameter D3 of the spherical portion 30. To significantly enhance electronically generated depictions of the sheath device 10 on a video display or the like, it has been found that forming D3 the diameter of the spherical portion 30 to be substantially 20 to 95 percent of the diameter of the first portion D1, and forming the diameter D2 of the annular recess, between 30 to 80 percent of the diameter D3 of the spherical portion 30 works well to yield a more discernable electronic image of the distal end of the body 11 of the sheath device 10. On such electronically generated images from sonic waves or RF energy communicated to the device 10 while withing the patient, a dimensioning of the diameter D2 of the annular recess 28 smaller than D3 the diameter of the spherical portion, causes the distal end 22 to be much more clearly visible on the display screen, at a wide variety of angles of the body 11 to the electronic sensor or the sonic generator for ultrasound.

Figure 4B:
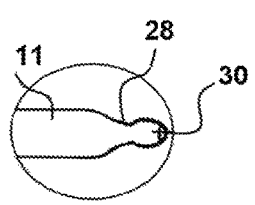
FIG. 4b shows the substantially spherical portion similar to that of FIG. 4a, but with more elongated sides to form a more substantially spherical shape, and which positions a curved wall surface extending radially around the second opening to the annular recess.

FIG. 4b shows the spherical portion 30 formed with an elongated circular or flattened spherical shape. This shape positions the preferred curved exterior surface radially extending around the second opening 20 as in all preferred modes of the device 10 herein. This curved surface extends radially from and around the second opening 20 toward the annular recess 28, which as noted is located in-between a linear first portion 13 of the body 11 and the spherical portion 30 of the body 11 of the sheath device 10.

Figure 4C:
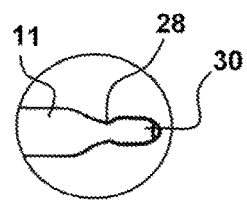
FIG. 4c depicts the substantially spherical portion similar to that of FIGS. 4a and 4b, but with a sidewall having a less pronounced curved surface, and which positions a curved end surface extending radially from the second opening toward the annular recess.

FIG. 4c depicts the spherical portion 30 formed with a more elongated circular or flattened spherical shape than that of FIG. 4b. This also guards against tissue lacerations and perforations, by positioning the curved exterior surface radially extending around the second opening 20, as in all preferred modes of the device 10 herein. This curved surface extends radially from the second opening 20 toward the annular recess 28, located in-between a linear first portion 13 of the body 11 and the spherical portion 30 of the body 11 of the sheath device 10.

Figure 5:
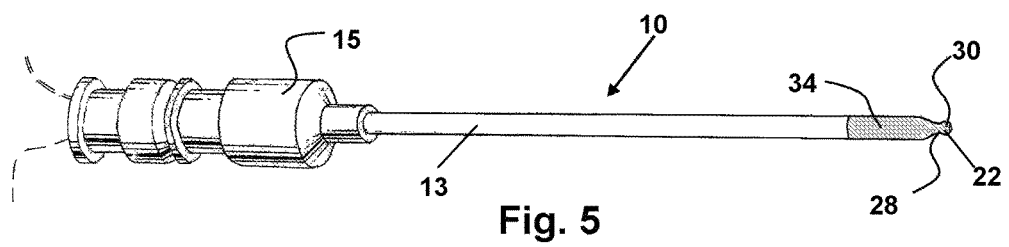
FIG. 5 depicts the exterior surface of the sheath at and adjacent the distal end, configured with a surfacing of the exterior surface adapted to enhance a sonic, RF, or computer aided electronic video display depiction thereof.

FIG. 5 depicts the exterior surface of the body 11 of the sheath device 10 at and adjacent the distal end 22, configured with an exterior surfacing 34 placed on the exterior circumferential surface of the body 11 of the sheath device 10. This surfacing 34 better reflects RF energy or sonic waves, back to their receiving device to enhance a sonic, RF, or computer-aided video screen depiction thereof.

Figure 6:
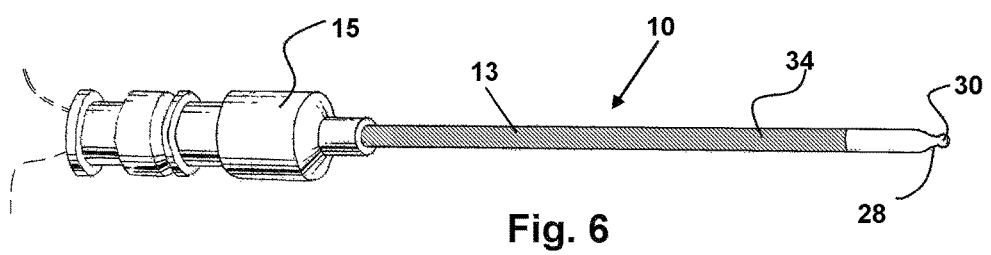
FIG. 6, depicts the exterior surface of the sheath at a first portion running toward the first end from the annular recess, configured with a surfacing adapted configured to enhance a sonic, RF, or computer generated video display depiction thereof.

FIG. 6, depicts the exterior surfacing 34 positioned on the exterior circumferential surface of the body 11 of the sheath device 10 along a section of the first portion 13 running from the annular recess 28 toward the first end 18. As with the surfacing of FIG. 5, it better reflects and or focuses or reacts with RF energy or sonic waves from a transducer, to enhance a sonic, RF, or computer aided depiction thereof, which as noted aids out of plane needle tip visualization as well as angles approaching or extending away from the viewer.

Such surfacing 34 can be formed of reflecting material for RF and sonic waves, from a group of reflective materials, including dimpled or otherwise structural surfacing of the exterior surface of the body 11, or a polymeric coating layer thereon which has nano particles such as nano glass or plastic microspheres encapsulated within the cured polymeric coating layer upon the exterior surface of the body 11 of the device 10.

While all of the fundamental characteristics and features of the neurovascular puncture-avoidant sheath invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed:

1. A sheath comprising:
 a body having an elongated cylindrical shape, said body formed in a unitary structure having a first end opposite a second end of said body;
 an axial passage communicating through said body along a straight line extending from a first opening formed in said body on said first end thereof to a second opening formed in said body at said second end of said body, said second opening fixed in an alignment with said first opening; said
 first end of said body adapted for an operative engagement with a handle having a needle projecting therefrom into said axial passage wherein in said operative engagement, manipulation of said handle translates a distal end of said needle to project from said second opening;
 an annular recess on an exterior surface said body adjacent said second end of said body;
 a substantially spherical portion of said body surrounding said axial passage and positioned said second end of said body adjacent said annular recess at a position in-between said annular recess and said second opening; and
 said spherical portion having a curved surface extending radially away from said second opening to an edge of said annular recess, whereby the needle with said handle in said operative engagement with said first end of said body, is protected from contact with body tissue until said manipulation of said handle translates said distal end of said needle to project from said second opening.

2. The sheath of claim 1 wherein said operative engagement of said first end of said body with a handle comprises threads formed into said axial passage at said first end of said body which are complimentary to threads formed on said handle of said needle.

3. The sheath of claim 2 wherein said spherical portion has a diameter which is between 20 to 95 percent of a diameter of a first portion of said body extending between said first end and said annular recess.

4. The sheath of claim 3 wherein said annular recess has a diameter sized between 30 to 80 percent of said diameter of said spherical portion.

5. The sheath of claim 4 additionally comprising:
a surfacing positioned on an exterior circumferential surface of said spherical portion of said body; and
said surfacing configured to enhance reflections of sound from a transducer employed to produce ultrasound images.

6. The sheath of claim 2 additionally comprising:
a surfacing positioned on an exterior circumferential surface of said spherical portion of said body; and
said surfacing configured to enhance reflections of sound from a transducer employed to produce ultrasound images.

7. The sheath of claim 1 wherein said operative engagement of said first end of said body with a handle comprises an interior surface of said axial passage at said first end of said body sized for a sliding frictional engagement with a surface on said handle surrounding said needle.

8. The sheath of claim 7 wherein said spherical portion has a diameter which is between 20 to 95 percent of a diameter of a first portion of said body extending between said first end and said annular recess.

9. The sheath of claim 8 wherein said annular recess has a diameter sized between 30 to 80 percent of said diameter of said spherical portion.

10. The sheath of claim 9 additionally comprising:
a surfacing positioned on an exterior circumferential surface of said spherical portion of said body; and
said surfacing configured to enhance reflections of sound from a transducer employed to produce ultrasound images.

11. The sheath of claim 8 additionally comprising:
a surfacing positioned on an exterior circumferential surface of said spherical portion of said body; and
said surfacing configured to enhance reflections of sound from a transducer employed to produce ultrasound images.

12. The sheath of claim 7 additionally comprising:
a surfacing positioned on an exterior circumferential surface of said spherical portion of said body; and
said surfacing configured to enhance reflections of sound from a transducer employed to produce ultrasound images.

13. The sheath of claim 1 wherein said spherical portion has a diameter which is between 20 to 95 percent of a diameter of a first portion of said body extending between said first end and said annular recess.

14. The sheath of claim 13 wherein said annular recess has a diameter sized between 30 to 80 percent of said diameter of said spherical portion.

15. The sheath of claim 14 additionally comprising:
a surfacing positioned on an exterior circumferential surface of said spherical portion of said body; and
said surfacing configured to enhance reflections of sound from a transducer employed to produce ultrasound images.

16. The sheath of claim 1 additionally comprising:
a surfacing positioned on an exterior circumferential surface of said spherical portion of said body; and
said surfacing configured to enhance reflections of sound from a transducer employed to produce ultrasound images.

17. A sheath comprising:
a rigid body having an elongated cylindrical shape, said body formed in a unitary structure having a first end opposite a second end of said body;
an axial passage communicating through said body from a first opening formed in said body on said first end thereof to a second opening in said second end of said body aligned with said first opening;
said first end of said body adapted for an operative engagement with a handle having a needle projecting therefrom into said axial passage wherein in said operative engagement, manipulation of said handle translates a distal end of said needle to project from said second opening;
an annular recess on an exterior surface of said body adjacent said second end thereof; said exterior surface of said body defining a substantially spherical portion of said body positioned; said spherical portion having a first side adjacent said annular recess and having a second side adjacent said second opening; and
said spherical portion having a curved surface extending radially away from said second side at said second opening to said first side adjacent said annular recess, whereby the needle with said handle in said operative engagement with said first end of said rigid body, is protected from contact with body tissue until said manipulation of said handle translates said distal end of said needle to project from said second opening.

18. The sheath of claim 17 wherein said spherical portion has a diameter which is between 30 to 80 percent of a diameter of a first portion of said body, said first portion of said body extending between said first end thereof and said annular recess.

* * * * *